United States Patent
Saito

(10) Patent No.: US 10,550,175 B2
(45) Date of Patent: Feb. 4, 2020

(54) MYCOPLASMA PNEUMONIAE IMMUNOLOGICAL DETECTION METHOD AND KIT

(71) Applicant: TAUNS CO., LTD., Shizuoka (JP)

(72) Inventor: Kenji Saito, Izunokuni (JP)

(73) Assignee: TAUNS CO., LTD., Shizuoka (JP)

( * ) Notice: Subject to any disclaimer, the term of this patent is extended or adjusted under 35 U.S.C. 154(b) by 0 days.

(21) Appl. No.: 16/193,909

(22) Filed: Nov. 16, 2018

(65) Prior Publication Data

US 2019/0085059 A1 Mar. 21, 2019

Related U.S. Application Data

(62) Division of application No. 14/913,612, filed as application No. PCT/JP2014/072068 on Aug. 22, 2014, now Pat. No. 10,174,103.

(30) Foreign Application Priority Data

Aug. 23, 2013 (JP) ................. 2013-173991

(51) Int. Cl.
*G01N 33/558* (2006.01)
*C07K 16/12* (2006.01)
*G01N 33/569* (2006.01)

(52) U.S. Cl.
CPC ....... *C07K 16/1253* (2013.01); *G01N 33/558* (2013.01); *G01N 33/56933* (2013.01); *G01N 2333/30* (2013.01); *G01N 2800/26* (2013.01)

(58) Field of Classification Search
None
See application file for complete search history.

(56) References Cited

U.S. PATENT DOCUMENTS

| | | |
|---|---|---|
| 4,945,041 A | 7/1990 | Baseman |
| 5,641,638 A | 6/1997 | Bredt et al. |
| 8,940,496 B2 | 1/2015 | Minagawa et al. |
| 2003/0039963 A1 | 2/2003 | Brahmachari et al. |
| 2012/0244544 A1 | 9/2012 | Minagawa et al. |
| 2017/0242007 A1 | 8/2017 | Tomiyama et al. |

FOREIGN PATENT DOCUMENTS

| | | |
|---|---|---|
| CN | 104198703 A | 12/2014 |
| JP | 63-298 A | 1/1988 |
| JP | 63-84484 A | 4/1988 |
| JP | 63-184064 A | 7/1988 |
| JP | 1-257264 A | 10/1989 |
| JP | 2011-220931 A | 11/2011 |
| JP | 2013-072663 A | 4/2013 |
| JP | 5331285 B2 | 10/2013 |
| JP | 5712140 B2 | 5/2015 |
| WO | 20021077183 A2 | 10/2002 |
| WO | 2009/072708 A1 | 6/2009 |
| WO | 20111068189 A1 | 6/2011 |
| WO | 2011/125606 A | 10/2011 |
| WO | 2016017598 A1 | 2/2016 |

OTHER PUBLICATIONS

EPO Office Action dated Feb. 28, 2018, EPO Application 14838384.7.
FEMS Microbiology Letters 198 (2001) 1-7.
Pediatrics of Japan, vol. 56, No. 6, 2015, p. 769-773.
Kodomo-no-Kansensho, vol. 3, No. 1, 2015, p. 32-33.
Gairai Shonika, vol. 18, No. 1, 2015, p. 134.
JPO Office Action apparently dated Mar. 13, 2018 re JP Application 2015-532927.
Chang et al., J.Bacteriol. Oct. 2011. 193(20): 5841-5846.
Varshney et al ., Clinical and Vaccine Immunology. Feb. 2008. 15(2): 215-220.
Hausner et al., Microbial Pathogenesis. Available online Aug. 13, 2013. vol. 64: 23-32.
JPO Office Action dated Dec. 2017, apparently on or about Dec. 19, 2017, in JP Appln. 2015-532927.
Office Action issued by JPO, in JP2015-532927, dated Oct. 6, 2017.
Dallo et al., Infect. Immun. 1990. 58: 4163-4165.
Lan et al, CN103275196-A-abstract only; Genbank accession No. BBA62138.
Greenspan et al., Nature Biotechnology 7: 936-937 (1999).
Chothia et al., The EMBO Journal, 1986, 514:823-26.
Layh-Schmitt, et al., "The adhesin related 30-kDa protein of Mycoplasma pneumoniae exhibits size and antigen variability," FEMS microbiology letters, 1997, pp. 101-108, vol. 152, No. 1.
Seto, et al., "Visualization of the attachment organelle and cytadherence proteins of Mycoplasma pneumoniae by Immunofluorescence microscopy," Journal of bacteriology, 2001, p. 1624, vol. 183, No. 5.
Intenational Search Report for PCT/JP20141/072068 dated Nov. 25, 2014; English Translation submitted herewith (4 Pages).
European Supplementary Search Report, dated Mar. 17, 2017, in EPO Appln. 14838384.7.
Chang et al., Domain Analysis of Protein P30 in Mycoplasma pneumoniae Cytadherence and Gliding Motility, Journal J. of Bacteriology, 193(7): 1726-1733 (Apr. 2011 ).

(Continued)

*Primary Examiner* — Jennifer E Graser
(74) *Attorney, Agent, or Firm* — Fitch, Even, Tabin & Flannery, LLP

(57) ABSTRACT

An object of the present invention is to provide a detection marker that can simply and rapidly detect *Mycoplasma pneumoniae*, which is a pathogen of *mycoplasma* pneumonia, at a high sensitivity, a specific antibody against the marker, and also an immunological detection method and a kit containing the antibody.

Infection with *Mycoplasma pneumoniae* can be rapidly and specifically diagnosed by producing an antibody specifically reactive to P30 protein of *Mycoplasma pneumoniae* and performing an immunological assay using the P30 protein as a detection marker. The present invention enables easy and rapid detection of *Mycoplasma pneumoniae* and diagnosis of infection with the bacteria at a hospital or the like without need of specialized instruments or skilled techniques.

7 Claims, 1 Drawing Sheet

Specification includes a Sequence Listing.

(56) References Cited

OTHER PUBLICATIONS

Dallo et al., Biofunctional Domains of the Mycoplasma pneumoniae P30 adhesion, Infection and Immunology, 64 (7):2595-2601 (Jul. 1996).

Morrison-Plummer et al., Biological Effects of Anti-Lipid and Anti-Protein Monoclonal Antibodies on Mycoplasma ; pneumoniae, Infection and Immunology, 53(2):398-403 (Aug. 1986).

Baseman et al., Identification of a 32-kilodalton Protein of Mycoplasma Pneumoniae Associated with Hemadsorption, Israel Journal of Medical Science, 23:474-479 (1987).

International Preliminary Examination Report for PCT/JP2014/072068, dated Nov. 25, 2014.

JPO Office Action dated Apr. 4, 2019, issued against JP Patent Application No. 2018-112308.

SEQUENCE LISTING

<160> NUMBER OF SEQ ID NOS: 2

<210> SEQ ID NO 1
<211> LENGTH: 274
<212> TYPE: PRT
<213> ORGANISM: Mycoplasma pneumoniae

<400> SEQUENCE: 1

```
Met Lys Leu Pro Pro Arg Arg Lys Leu Lys Leu Phe Leu Leu Ala Trp
1               5                   10                  15

Met Leu Val Leu Phe Ser Ala Leu Ile Val Leu Ala Thr Leu Ile Leu
            20                  25                  30

Val Gln His Asn Asn Thr Glu Leu Thr Glu Val Lys Ser Glu Leu Ser
        35                  40                  45

Pro Leu Asn Val Val Leu His Ala Glu Glu Asp Thr Val Gln Ile Gln
    50                  55                  60

Gly Lys Pro Ile Thr Glu Gln Ala Trp Phe Ile Pro Thr Val Ala Gly
65                  70                  75                  80

Cys Phe Gly Phe Ser Ala Leu Ala Ile Ile Leu Gly Leu Ala Ile Gly
                85                  90                  95

Leu Pro Ile Val Lys Arg Lys Glu Lys Arg Leu Leu Glu Glu Lys Glu
            100                 105                 110

Arg Gln Glu Gln Leu Ala Glu Gln Leu Gln Arg Ile Ser Ala Gln Gln
        115                 120                 125

Glu Glu Gln Gln Ala Leu Glu Gln Gln Ala Ala Ala Glu Ala His Ala
    130                 135                 140

Glu Ala Glu Val Glu Pro Ala Pro Gln Pro Val Pro Val Pro Pro Gln
145                 150                 155                 160

Pro Gln Val Gln Ile Asn Phe Gly Pro Arg Thr Gly Phe Pro Pro Gln
                165                 170                 175

Pro Gly Met Ala Pro Arg Pro Gly Met Pro Pro His Pro Gly Met Ala
            180                 185                 190

Pro Arg Pro Gly Phe Pro Pro Gln Pro Gly Met Ala Pro Arg Pro Gly
        195                 200                 205

Met Pro Pro His Pro Gly Met Ala Pro Arg Pro Gly Phe Pro Pro Gln
    210                 215                 220

Pro Gly Met Ala Pro Arg Pro Gly Met Pro Pro His Pro Gly Met Ala
225                 230                 235                 240

Pro Arg Pro Gly Phe Pro Pro Gln Pro Gly Met Ala Pro Arg Pro Gly
                245                 250                 255

Met Gln Pro Pro Arg Pro Gly Met Pro Pro Gln Pro Gly Phe Pro Pro
            260                 265                 270

Lys Arg
```

<210> SEQ ID NO 2
<211> LENGTH: 201
<212> TYPE: PRT
<213> ORGANISM: Mycoplasma pneumoniae

<400> SEQUENCE: 2

```
Phe Ile Pro Thr Val Ala Gly Cys Phe Gly Phe Ser Ala Leu Ala Ile
1               5                   10                  15

Ile Leu Gly Leu Ala Ile Gly Leu Pro Ile Val Lys Arg Lys Glu Lys
            20                  25                  30
```

```
Arg Leu Leu Glu Glu Lys Glu Arg Gln Glu Gln Leu Ala Glu Gln Leu
        35              40              45
Gln Arg Ile Ser Ala Gln Gln Glu Glu Gln Gln Ala Leu Glu Gln Gln
    50              55              60
Ala Ala Ala Glu Ala His Ala Glu Ala Glu Val Glu Pro Ala Pro Gln
65              70              75              80
Pro Val Pro Val Pro Pro Gln Pro Gln Val Gln Ile Asn Phe Gly Pro
                85              90              95
Arg Thr Gly Phe Pro Pro Gln Pro Gly Met Ala Pro Arg Pro Gly Met
                100             105             110
Pro Pro His Pro Gly Met Ala Pro Arg Pro Gly Phe Pro Pro Gln Pro
        115             120             125
Gly Met Ala Pro Arg Pro Gly Met Pro Pro His Pro Gly Met Ala Pro
        130             135             140
Arg Pro Gly Phe Pro Pro Gln Pro Gly Met Ala Pro Arg Pro Gly Met
145             150             155             160
Pro Pro His Pro Gly Met Ala Pro Arg Pro Gly Phe Pro Pro Gln Pro
                165             170             175
Gly Met Ala Pro Arg Pro Gly Met Gln Pro Pro Arg Pro Gly Met Pro
                180             185             190
Pro Gln Pro Gly Phe Pro Pro Lys Arg
        195             200
```

MYCOPLASMA PNEUMONIAE IMMUNOLOGICAL DETECTION METHOD AND KIT

CROSS-REFERENCE TO RELATED APPLICATIONS

This application is a divisional application of U.S. application Ser. No. 14/913,612, filed Feb. 22, 2016, which is the U.S. National Stage Application filed under 35 U.S.C. § 371 of International Application PCT/JP2014/072068, filed Aug. 22, 2014, designating the United States, claims priority from Japanese Patent Application 2013-173991, filed Aug. 23, 2013, and the complete disclosures of all such prior applications, including sequence listing(s), are hereby incorporated herein by reference in their entirety for all purposes.

TECHNICAL FIELD

The present invention relates to an antibody against P30 protein of *Mycoplasma pneumoniae*, and an immunological method and a kit for detecting *Mycoplasma pneumoniae* using the antibody.

BACKGROUND ART

*Mycoplasma* pneumonia is atypical pneumonia caused by *Mycoplasma pneumoniae*. *Mycoplasma* pneumonia, together with *chlamydia* pneumonia, constitutes 30% to 40% of the atypical pneumonia cases and also constitutes a high percentage of the community-acquired pneumonia cases.

*Mycoplasma* pneumonia is common in infants, children, and adolescence. The incubation period is 2 to 3 weeks. Excretion of the pathogen into respiratory mucosa is observed in 2 to 8 days before the onset of initial symptom, becomes the highest at the onset of clinical symptoms, continues at a high level for about one week, and then further continues for 4 to 6 weeks or more. Main clinical symptoms are fever, general malaise, headache, and other cold-like symptoms. *Mycoplasma* pneumonia is characterized by, for example, high fever greater than 38° C. and intense dry cough. The cough further continues for a long time, 3 to 4 weeks, after decline of fever. However, there is no examination finding characteristic to *mycoplasma* pneumonia, and pale ground-glass appearance in chest X-ray examination is typical.

The manner of infection with *Mycoplasma* is droplet infection and contact infection from an infected patient. *Mycoplasma pneumoniae* invades the respiratory tract and attaches to the bronchi or bronchiole epithelium to achieve the infection.

*Mycoplasma* infection is designated as a notifiable infectious disease (Infectious diseases Category V) based on the Infectious Diseases Control Law, and designated medical care providers have an obligation to promptly report the number of patients.

*Mycoplasma* is a minimum microorganism that can replicate itself, and differs from other bacteria in that it does not have a cell wall. Accordingly, β-lactam antibiotics and cephem antibiotics, which are antibiotics having a function of inhibiting cell wall synthesis, are ineffective, and an administration of macrolide antibiotics, tetracycline antibiotics and new quinolone antibiotics is required for treatment. Prompt identification of the pathogen is therefore necessary for determining the initial treatment plan.

At present, *Mycoplasma pneumoniae* infection is definitely diagnosed by an isolation culture method and a serological test.

The isolation culture needs a specialized culture medium (PPLO medium) for detecting *Mycoplasma*. In addition, its proliferation is slow, compared to other bacteria, thereby taking at least about one week for obtaining the result of determination. It is therefore difficult to rapidly identify the pathogen by the isolation culture method in clinical sites.

*Mycoplasma* is susceptible to temperature, and samples containing *Mycoplasma* cannot be kept in cold storage, unlike samples containing common bacteria. Accordingly, *Mycoplasma* contained in a sample may become extinct or decrease during storage or transportation of the sample and may not be detected even by the isolation culture method.

Examples of the serological test include an indirect hemagglutination (IHA) test, a particle agglutination (PA) method, and an enzyme immunoassay (EIA), which specifically detect IgG antibody or IgM antibody.

Furthermore, an immunochromatographic kit (Immuno-Card *Mycoplasma* Antibody, available from TFB, Inc.) is commercially available as a simple test detecting *Mycoplasma pneumoniae*-specific IgM antibody in serum or plasma by EIA and is used at clinical sites.

In the serological test, although the IgM antibody in a sample to be detected increases at the early stage of infection, the sample may show false negative in the case of low antibody production response or depending on assay timing. Furthermore, since it takes a long time before IgM antibody disappears in blood, it cannot be said that the result of the serological test always correctly indicates the current infection status.

Accordingly, definite diagnosis by the serological test needs quantitative tests using paired sera of acute and convalescent stages, and therefore has to be ex-post diagnosis in many cases.

A nucleic acid detection method for detecting DNA of *Mycoplasma pneumoniae* is also employed. In the detection method, however, the procedure of amplifying nucleic acid is complicated and needs specialized equipment, and the assay takes several hours. Thus, the method is not a test that is generally used.

In order to more rapidly and simply detect *Mycoplasma pneumoniae* infection, specific antibody against *Mycoplasma pneumoniae* antigen has been developed, and a detection method of distinguishing whether *mycoplasma* infection is present or not has been reported.

*Mycoplasma pneumoniae* attaches itself to the respiratory epithelial cell cilia with its adhesive organ in a form of a flask-shaped protrusion, and then moves to the cell surface by gliding motility and adheres thereto to achieve the infection. Production of an antibody specific to P1 protein (169 KDa), which is known as adhesive protein playing a central role in this adhesion or gliding motility, and a detection method using the P1 protein as a detection marker have been reported (Patent Documents 1 and 2).

It is also known that P1 protein, the antigen to be detected reported in the above reports, has two genotypes and that the amino acid sequences corresponding to the genotypes of P1 protein are different from each other. Accordingly, in order to broadly detect *Mycoplasma pneumoniae*, production of each antibody against P1 protein of each P1 genotype or an antibody recognizing a common site of P1 protein of the different genotypes is necessary. In addition, seasonal epidemic has been reported such that a genotype different from the epidemic genotype in the latest season is detected, that is, the genotype changes depending upon epidemic seasons.

Therefore, it is necessary to find out the genotype at an early stage of the epidemic and use an antibody specific thereto.

A detection method using DnaK protein, which is known to be conserved among isolated strains of *Mycoplasma pneumoniae* compared with P1 protein, as a detection marker (Patent Literature 3) has been also reported. However, *Mycoplasma genitalium* causing human urinary infectious diseases also has DnaK protein, and therefore also shows reactivity in the detection method. Consequently, *Mycoplasma pneumoniae* cannot be specifically detected by using the above protein as a detection marker.

If *mycoplasma* pneumonia is not appropriately treated, the symptoms may be protracted or become severe or may further cause the spread of the infection due to secondary infection. Accordingly, in order to select appropriate treatment and antibiotics, rapid and conclusive detection of *Mycoplasma pneumoniae* is demanded.

Furthermore, even though specific and rapid detection of *Mycoplasma pneumoniae* has been contemplated, a detection marker that can further specifically detect *Mycoplasma pneumoniae*, a specific antibody against the marker, and also an immunoassay and a kit containing the antibody have been demanded.

CONVENTIONAL TECHNICAL DOCUMENTS

Patent Documents

Patent Document 1: Japanese Patent Laid-Open No. H5-304990
Patent Document 2: Japanese Patent Laid-Open No. 2013-72663
Patent Document 3: International Publication No. WO2011/068189

Non-Patent Documents

Non Patent Document 1: D. Nakane, et al., "Isolation and Characterization of P1 Adhesin, a Leg Protein of the Gliding Bacterium *Mycoplasma pneumoniae*", Journal of Bacteriology, February 2011, pp. 715-722

SUMMARY OF INVENTION

Problem to be Solved by the Invention

The purpose of the present invention is to provide a detection marker that can simply and rapidly detect *Mycoplasma pneumoniae*, which is a pathogen of *mycoplasma* pneumonia, at a high sensitivity, a specific antibody against the marker, and also an immunological detection method and a kit containing the antibody.

Means for Solving the Problem

The present inventor has made a diligent investigation under the above-described circumstance and as a result, found out that P30 protein, which is one of adhesion factors of *Mycoplasma pneumoniae*, is commonly conserved among isolated strains and is a specific and useful detection marker, and arrived at the completion of the present invention.

That is, according to one aspect of the present invention, there is provided an immunological method of detecting *Mycoplasma pneumoniae* characterized by using an antibody against P30 protein of *Mycoplasma pneumoniae*.

According to another aspect of the present invention there is provided an immunoassay kit for *Mycoplasma pneumoniae*, comprising at least an antibody against P30 protein of *Mycoplasma pneumoniae*.

In particular, the immunological detection method is preferably an enzyme-linked immunosorbent assay (ELISA) or an immunochromatographic assay, etc.

Further, according to another aspect of the present invention, there is provided an immunological method of detecting *Mycoplasma pneumoniae* using an antibody recognizing an epitope of P30 protein present in a region of the amino acid sequence of SEQ ID NO: 2.

Further, according to another aspect of the present invention, there is provided an immunological method of detecting *Mycoplasma pneumoniae* by a sandwich immunoassay using first and second antibodies against P30 protein of *Mycoplasma pneumoniae*.

Further, according to another aspect of the present invention, there is provided a sandwich immunoassay kit for *Mycoplasma pneumoniae*, comprising at least first and second antibodies against P30 protein of *Mycoplasma pneumoniae*.

In particular, the sandwich immunoassay is preferably an enzyme-linked immunosorbent assay (ELISA)) or an immunochromatographic assay, etc.

According to a preferred embodiment of the present invention, there is provided an immunochromatographic assay for detecting *Mycoplasma pneumoniae*, comprising:

providing a membrane carrier having a capturing zone which is formed by previously immobilizing a first antibody against P30 protein of *Mycoplasma pneumoniae* at a predetermined position;

chromatographically developing a liquid mixture in the membrane carrier toward the capturing zone, said liquid mixture containing a second antibody against the P30 protein and a predetermined amount of a test sample, whereby a complex of an antigen contained in the test sample and the second antibody is captured by the capturing zone.

According to another preferred embodiment of the present invention, there is provided a *Mycoplasma pneumoniae*-detecting immunochromatographic test strip, at least comprising first and second antibodies against P30 protein of *Mycoplasma pneumoniae* and a membrane carrier, wherein the first antibody is previously immobilized at a predetermined position of the membrane carrier so as to form a capturing zone; and the second antibody is labeled with an appropriate labeling substance and is provided at a position separated from the capturing zone so as to be chromatographically developed in the membrane carrier.

Although the antibody against the P30 protein, which is essentially used in the present invention, may be a polyclonal antibody or a monoclonal antibody, preferred is a monoclonal antibody from the viewpoint of reaction specificity.

According to still another aspect, the antibody which is essentially used in the present invention recognizes an epitope of the P30 protein present in a region of the amino acid sequence of SEQ ID NO: 2. Similarly, from the viewpoint of reaction specificity, preferred is a monoclonal antibody. The amino acid sequence of SEQ ID NO: 2 constitutes a part of the entire amino acid sequence of the P30 protein set forth in SEQ ID NO: 1 and is a region containing an epitope present in the P30 protein.

In a sandwich immunoassay such as immunochromatographic assay, although the first and second antibodies used therein may be each a polyclonal antibody or a monoclonal antibody, from the viewpoint of reaction specificity, generally speaking, at least one of the antibodies is preferably a monoclonal antibody, and both antibodies are particularly preferably monoclonal antibodies. In addition, a large number of P30 protein molecules are present and are localized on the cell surface. In order to avoid competition between antibodies and to obtain higher reactivity, the first antibody and the second antibody preferably recognize different epitopes present on the P30 protein.

Incidentally, the P30 protein of *Mycoplasma pneumoniae* to which the antibody for detecting *Mycoplasma pneumoniae* according to the present invention reacts is a protein necessary for adhesion of *Mycoplasma* to a host cell and is known as one of the accessory proteins that work together with an adhesion factor P1 protein.

The P30 protein has a molecular weight of 30 KDa and is one of the adhesive proteins involved in adhesion and pathogenicity, like P1 protein. In the *Mycoplasma pneumoniae* cell, the P30 protein is localized on the cell surface at an end of the adhesive organ and is a transmembrane protein having the N-terminal embedded in the cell membrane and the C-terminal present outside the cell membrane. The P30 protein includes an amino acid sequence containing a large number of proline on the C-terminal side and has a repeating structure of the amino acid sequence containing a large number of proline. In general, a region having an amino acid sequence containing proline is known to form a three-dimensional conformation and is known to have a possibility of becoming an epitope reactive with an antibody.

Accordingly, the antibody used in the present invention is likely to be an antibody recognizing a site having the repeating structure of the amino acid sequence containing a large number of proline in an extracellular region of P30 protein. In addition, the amino acid sequence of SEQ ID NO: 2 is believed to be the amino acid sequence constituting the extracellular region and to be a region including the region having the repeating structure of the amino acid sequence containing a large number of proline and including an epitope of P30 protein.

Thus, according to another aspect of the present invention, there is provided an antibody recognizing P30 protein of *Mycoplasma pneumoniae*, and further there is provided an antibody recognizing an epitope of P30 protein present in a region of the amino acid sequence of SEQ ID NO: 2.

Effect of Invention

According to the present invention, infection with *Mycoplasma pneumoniae* can be rapidly and specifically diagnosed by producing an antibody specifically reactive to P30 protein of *Mycoplasma pneumoniae* and performing an immunological detection using the P30 protein of *Mycoplasma pneumoniae* as a detection marker. The immunological detection method and assay apparatus of the present invention enables the detection of *Mycoplasma pneumoniae* and the diagnosis of infection with the bacteria to be made simply and rapidly at a hospital or another facility without need of any specialized equipment or skill.

DESCRIPTION OF EMBODIMENTS

Figure 1A:
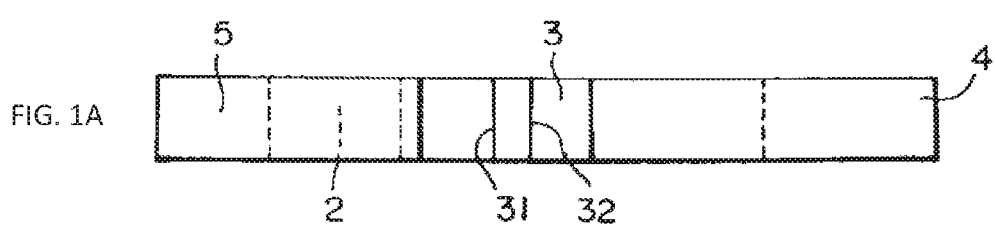
FIG. 1A is a plan view of an immunochromatographic test strip.

In the present invention, each step in production of an antibody and detection or assay method using the antibody is performed in conformity with each immunological procedure known per se.

(Antibody)

A polyclonal antibody specific to P30 protein of *Mycoplasma pneumoniae* can be prepared by, for example, extracting and purifying P30 protein from *Mycoplasma pneumoniae* cells or extracting and purifying P30 protein expressed from a cloned gene for P30 protein by genetic engineering in a host such as *Escherichia coli*; immunizing an animal with the extracted and purified P30 protein or a polypeptide as a part of P30 protein, as an antigen for immunization, in accordance with an ordinary method; and then obtaining the polyclonal antibody from the antiserum of the immunized animal.

A monoclonal antibody specific to P30 protein of *Mycoplasma pneumoniae* can be prepared by, for example, immunizing an animal, such as a mouse, with P30 protein extracted and purified from *Mycoplasma pneumoniae* cells or P30 protein expressed by genetic engineering or a polypeptide as a part of P30 protein as mentioned above, as an antigen for immunization; fusing the spleen cells of the immunized animal and myeloma cells; selecting hybridomas in a HAT-containing medium and growing the hybridomas; and screening the grown strains with P30 protein prepared as above by, for example, an enzyme immunoassay for a strain producing an anti-P30 protein antibody.

Examples of the antibody of the present invention include antibodies, and antibody fragments and modified antibodies substantially equivalent to the antibodies against P30 protein of *Mycoplasma pneumoniae*. Examples of the antibody fragments include Fab fragments, F(ab')$_2$ fragments, Fab' fragments, and scFv fragments. Furthermore, a P30 protein-binding polypeptide derived from the antibody is also encompassed in the antibody of the present invention.

The immunochromatographic assay of the present invention for detecting *Mycoplasma pneumoniae* in a test sample can be practiced easily in accordance with the structure of a known immunochromatographic test strip.

Generally, such an immunochromatographic test strip is constituted by at least a first antibody which is capable of undergoing antigen-antibody reaction at a first antigenic determinant of an antigen, a second antibody which is labeled and capable of undergoing antigen-antibody reaction at a second antigenic determinant of the antigen, and a membrane carrier, wherein the first antibody is previously immobilized in a predetermined position of the membrane carrier so as to form a capturing zone, and the second antibody is placed at a position separated from the capturing zone so as to be allowed to be chromatographically developed in the membrane carrier. Although the first antibody and the second antibody may be each a polyclonal antibody or a monoclonal antibody as described above, at least one of them is preferably a monoclonal antibody. The first antibody and the second antibody are generally used in a "hetero" combination. That is, the first and second antibodies which recognize the respective antigenic determinants different in both position and conformation on an antigen are used in combination. However, the first antigenic determinant and the second antigenic determinant may have the same conformation as long as they are different in position on the antigen, and in such a case, the first antibody and the second antibody may be monoclonal antibodies in a "homo" combination, that is, one and the same monoclonal antibody can be used as both the first antibody and the second antibody.

Figure 1B:
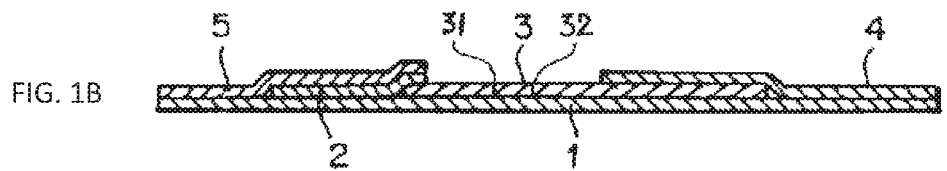
FIG. 1B is a vertical cross-sectional view of the immunochromatographic test strip shown in FIG. 1A.

As a specific example, mention may be made of a test strip as shown in FIG. 1. In FIG. 1, the numeral 1 indicates an adhesive sheet, 2 indicates an impregnated member, 3 indicates a membrane carrier, 31 indicates a capturing zone, 32 indicates a control capturing zone, 4 indicates an absorbing member, and 5 indicates a sample-receiving member.

In the example shown in the drawing, the membrane carrier 3 consists of an elongated strip-shaped nitrocellulose membrane filter having a width of 5 mm and a length of 36 mm.

In the membrane carrier 3, a first antibody is immobilized at a position of 7.5 mm from the end on the starting side of chromatographic development, so as to form a capturing zone 31 of an analyte. Furthermore, the membrane carrier 3 is provided with a control capturing zone 32 at a position of 15 mm from the end on the starting side of chromatographic development. This control capturing zone 32 is provided for verifying whether the reaction is performed or not regardless of the presence or absence of an analyte and can be usually formed by immobilizing a material (excluding the analyte) specifically immunologically binding to the second antibody to the membrane carrier 3. For example, when an antibody derived from a mouse is used as the second antibody, an antibody against the mouse antibody can be used.

In the example shown in the figure, a nitrocellulose membrane filter is used as the membrane carrier 3. However, any type of membrane carrier can be used herein, as long as it is able to chromatographically develop an analyte contained in a test sample and immobilize an antibody that forms the capturing zone 31. Thus, other types of cellulose membranes, nylon membranes, glass fiber membranes, or the like can also be used.

The impregnation member 2 comprises a member impregnated with a second antibody that undergoes antigen-antibody reaction with the antigen at a second antigenic determinant located at a site different from the first antigenic determinant to which the first antibody binds. The second antibody is previously labeled with an appropriate labeling substance.

In the example as shown in the figure, a strip-shaped glass fiber nonwoven fabric having a size of 5 mm×15 mm is used as the impregnated member 2. However, the impregnated member 2 is not limited thereto, but includes, for example, cellulose fabrics (a filter paper, a nitrocellulose membrane, etc.), porous plastic fabrics such as of polyethylene and polypropylene, and others.

As a labeling substance that labels the second antibody, any substance can be used, as long as it is usable herein. Examples of such a labeling substance include a color labeling substance, and an enzyme labeling substance, and a radiation labeling substance. Of these, a color labeling substance is preferably used because observation of a color change in the capturing zone 31 with naked eyes enables rapid and simple determination.

Examples of the color labeling substance include colloidal metals, such as colloidal gold and colloidal platinum; colloidal complexes of these metals; and latexes, such as synthetic latexes such as polystyrene latexes colored with pigments such as red and blue pigments and natural rubber latexes. Among these, colloidal metals, such as colloidal gold, are particularly preferred.

The impregnation member 2 can be produced, for example, by impregnating a member, such as the above-mentioned glass fiber non-woven fabric, with a suspension of a labeled second antibody and drying it.

As shown in FIG. 1, the immunochromatographic test strip of the present invention can be produced as follows. The membrane carrier 3 is affixed to the middle of the adhesive sheet 1. On the end on the starting side of chromatographic development (that is, the left side in FIG. 1 which is hereinafter referred to as an "upstream side" whilst the opposite side, that is, the right side in FIG. 1 is hereinafter referred to as a "downstream side") of the membrane carrier 3, the downstream side end of the impregnated member 2 is laid so as to communicate them. The upstream side zone of the impregnated member 2 is affixed to the adhesive sheet 1.

Moreover, if necessary, the downstream side zone of a sample-receiving member 5 may be placed on the upper face of the impregnated member 2 whilst the upstream side zone of the sample-receiving member 5 may also be affixed to the adhesive sheet 1. Furthermore, the upstream side zone of an absorbing member 4 may be placed on the upper face of the downstream side zone of the membrane carrier 3 whilst the downstream side zone of the absorbing member 4 may be affixed to the adhesive sheet 1.

The absorbing member 4 may be made of any material as long as it is able to quickly absorb and retain a liquid. Examples of such a material include cotton fabrics, filter paper, and porous plastic nonwoven fabrics made from polyethylene, polypropylene, etc. In particular, filter paper is optimal.

As the sample-receiving member 5, may be used, for example, a sheet or film of a porous synthetic resin such as porous polyethylene and porous polypropylene, or cellulose paper or a woven or nonwoven fabric such as a filter paper and a cotton fabric.

Thus, a test sample containing a biological sample or the like is, if required, mixed with a suitable developing solvent so as to obtain a liquid mixture that can be developed chromatographically. Thereafter, the liquid mixture is injected into the sample-receiving member 5 of the immunochromatographic test strip as shown in FIG. 1, so that it passes through the sample-receiving member 5 and is mixed with a labeled second antibody at the impregnated member 2.

Furthermore, the immunochromatographic test strip shown in FIG. 1 can be provided in a state of being accommodated in an appropriate plastic case having a test sample injection portion and a determination portion which are respectively opened above the sample-receiving member 5 and the capturing zone 31. In order to prevent secondary infection of a user, the immunochromatographic test strip is preferably provided in a state being accommodated in the plastic case.

Thus, a test sample containing a biological sample or the like is, if required, mixed with a suitable developing solvent so as to obtain a liquid mixture that can be developed chromatographically. Thereafter, the liquid mixture is injected into the sample-receiving member 5 of the immunochromatographic test strip as shown in FIG. 1, so that it passes through the sample-receiving member 5 and is mixed with a labeled second antibody at the impregnated member 2.

In this instance, if an analyte exists in the aforementioned liquid mixture, a complex of the analyte and the second antibody is formed as a result of antigen-antibody reaction. This complex is developed chromatographically in the membrane carrier 3, and then reaches the capturing zone 31 and is captured by the first antibody immobilized therein as a result of antigen-antibody reaction.

In this instance, if a color labeling substance such as colloidal gold is used as a labeling substance, the analyte can be immediately determined qualitatively or quantitatively based on coloring caused by accumulation of the color labeling substance at the capturing zone 31. Furthermore, the intensity of the coloring can be digitized and can be quantitatively measured by optically reading the intensity of the coloring of the color labeling substance accumulated on the capturing zone 31 of the immunochromatographic test strip with an immunochromatography reader.

In addition, when the chromatographic development is normally performed, the second antibody not involved in the antigen-antibody reaction with the analyte reaches the control capturing zone 32 and is captured by an antibody that is immobilized therein and reactive to the second antibody. On this occasion, if a color labeling substance is used as a labeling substance, the control capturing zone 32 colors by accumulation of the color labeling substance to confirm that the chromatographic development has been normally performed. In contrast, if the control capturing zone 32 does not color, it indicates that a problem such as no development of the second antibody happens.

In the immunochromatographic test strip shown in the figure, the second antibody is impregnated in the impregnating member 2 and is disposed on the membrane carrier 3. The second antibody is not limited to the configuration shown in the figure and may be provided at a position separated from the capturing zone 31 so as to be developed chromatographically in the membrane carrier 3. For example, the second antibody may be enclosed in advance in a container such as a tube provided for mixing a test sample with a developing solvent and may be packaged together with a test strip including the membrane carrier 3 on which the first antibody is immobilized in advance.

Any test sample can be used. For example, it may be a biological sample in which *Mycoplasma pneumoniae* may be present, such as nasal cavity aspirate, nasal cavity swab, throat swab, sputum, saliva, and bronchial washings. The test sample may be diluted with an appropriate diluent such as a developing solvent before it is applied to the membrane carrier. Furthermore, after removal of viscous substance or solids derived from biological components contained in a test sample by filtration with a filter, the test sample may be applied to the membrane carrier.

When a test sample contaminated with blood is used in a test, in particular, using an antibody labeled with a color labeling substance such as colloidal gold, a hematocyte-capturing membrane member is preferably disposed on the sample receiving member. The hematocyte-capturing membrane member is preferably laminated between the aforementioned impregnated member and the aforementioned sample-receiving member. This inhibits development of erythrocytes in the membrane carrier and thus facilitates the confirmation of accumulation of color labeling substances in the capturing zone of the membrane carrier. As such a hematocyte-capturing membrane member, a carboxymethyl cellulose membrane is used. Specifically, an ion exchange filter paper CM (trade name) available from Advantec Toyo K.K., an ion exchange cellulose paper available from Whatman Japan K.K., etc. can be used.

EXAMPLES

The present invention will be described more specifically by way of the following examples, but is not limited to the examples.

Example 1: Expression and Purification of Recombinant P30 Protein

The amino acid sequence of P30 protein of *Mycoplasma pneumoniae* M129 strain was obtained from a database of DNA Data Bank of Japan (DDBJ). An extracellular region excluding a transmembrane domain, the amino acid sequence (AA74-274) set forth in SEQ ID NO: 2, was specified from the amino acid sequence of the P30 protein, and a gene sequence corresponding to the amino acid sequence was synthesized. A His-tag expression vector, pET302/NT-His, was cleaved with a restriction enzyme, EcoRI, was then dephosphorylated using an alkaline phosphatase, and was mixed with the gene sequence, followed by a ligation reaction using DNA Ligation Kit Ver. 2 (Takara Bio Inc.). A recombinant P30 plasmid carrying the target gene was introduced into a recombinant protein-expressing host, *E. coli* BL (DE3) pLysS (Novagen). The host bacteria were cultured in an LB agar plate medium. The resulting colonies were cultured in an LB liquid medium. Subsequently, 1 mM IPTG (Takara Bio Inc.) was added to the medium to induce expression of recombinant P30 protein, and *E. coli* was then collected. The collected bacteria were resuspended in a solubilization buffer (0.5% Triron X-100 (Sigma), 10 mM imidazole, 20 mM phosphate, and 0.5 M NaCl (pH 7.4) (Amersham)) and were solubilized by ultrasonication. The recombinant P30 protein was then purified with His trap Kit (Amersham). This purified protein was dialyzed against a phosphate buffered saline (hereinafter, referred to as PBS) to obtain a target recombinant P30 protein.

Example 2: Production of Monoclonal Antibody Against Recombinant P30 Protein

The recombinant P30 protein prepared in Example 1 was used as an antigen for immunization to produce a monoclonal antibody against the recombinant P30 protein (hereinafter, referred to as anti-P30 antibody). The monoclonal antibody was produced in accordance with an ordinary method. The recombinant P30 protein (100 μg) was mixed with an equal amount of Complete Freund's Adjuvant (Difco). A mouse (BALB/c, 5 weeks old, Japan SLC, Inc.) was immunized with the mixture three times, and the spleen cells of the mouse were used in cell fusion using Sp2/0-Ag14 mouse myeloma cells (Shulman, et al., 1978). The cells were cultured in a culture solution prepared by adding L-glutamine (0.3 mg/mL), penicillin G potassium (100 unit/mL), streptomycin sulfate (100 μg/mL), and Gentacin (40 μg/mL) to Dulbecco's Modified Eagle Medium (DMEM) (Gibco) and also adding fetal calf serum (JRH) thereto in an amount of 10%. The cell fusion was performed by mixing immunized mouse spleen cells with Sp2/0-Ag14 cells and adding polyethylene glycol solution (Sigma) to the mixture. The hybridomas were cultured in HAT-DMEM (serum-added DMEM containing 0.1 mM sodium hypoxanthine, 0.4 μM aminopterin, and 0.016 mM thymidine (Gibco)). Antibody production in the culture supernatant was verified by enzyme-linked immunosorbent assay (ELISA). Antibody production-positive cells were cultured in HT-DMEM (serum-added DMEM containing 0.1 mM sodium hypoxanthine and 0.16 mM thymidine) and were further continuously cultured in serum-added DMEM.

Example 3: Preparation of Monoclonal Antibody

A mouse (BALB/c, retired, Japan SLC, Inc.), inoculated with 2,6,10,14-tetramethylpentadecane (Sigma) in advance, was intraperitoneally inoculated with the cloned cells, and the ascites was collected. The ascites was applied to a protein G column to purify a monoclonal antibody. The isotype of the produced monoclonal antibody was identified by Mouse Monoclonal Antibody Isotyping Reagents (Sigma).

Eventually, five clones of cells producing monoclonal antibodies against P30 protein were obtained. All these monoclonal antibodies were of $IgG_1$ immunoglobulin isotype.

Reference Example 1: Production of Standard Bacterial Solution for Test

PPLO media were inoculated with standard strains of *Mycoplasma pneumoniae* M129 strain and FH strain, followed by culturing in an atmosphere of 5% $CO_2$ at 37° C. until the desired concentration was obtained. The resulting culture solution was 10-fold serially diluted with a PPLO liquid medium until giving 100000-fold diluted solution. The number of grown colonies in each diluted solution on the PPLO agar medium was counted under a stereomicroscope to calculate the bacterial concentration. The resulting culture solutions were used as bacterial solutions for tests.

Comparative Example 1: Purification of *Mycoplasma pneumoniae* P1 Protein

A PPLO liquid medium was inoculated with a *Mycoplasma pneumoniae* M129 strain, followed by culturing at 37° C. The resulting culture solution was centrifuged to collect the cells. P1 protein was purified from the cells in accordance with the method of Nakane, et al. (Journal of Bacteriology, 2011).

The resulting cells were washed with a phosphate buffered saline, pH 7.4, (hereinafter, referred to as PBS) twice. The cells were suspended in a PBS containing 1% CHAPS, and the suspension was centrifuged. The resulting sediment was then dissolved in a PBS containing 2% octylglucoside. The solution was centrifuged, and the supernatant was collected. The resulting supernatant was subjected to ammonium sulfate fractionation, followed by centrifugation. The resulting sediment was dissolved in a PBS containing 0.3% Triton X-100, and the solution was purified by gel filtration column chromatography using Superdex 200. The fraction containing the purified protein was analyzed by SDS-page to confirm a single band at about 170 kDa. Thus, target P1 protein was obtained.

Similarly, P1 protein derived from *Mycoplasma pneumoniae* FH strain was purified from cells to obtain target P1 protein.

Comparative Example 2: Production of Monoclonal Antibody Against P1 Protein

The purified P1 protein prepared in Comparative Example 1 was used as an antigen for immunization, and a monoclonal antibody against P1 protein (hereinafter, referred to as anti-P1 antibody) was produced. The monoclonal antibody was produced in conformity with the method described in Example 2. The resulting cells were screened for anti-P1 antibody-producing cells by enzyme-linked immunosorbent assay (hereinafter, referred to as ELISA) using the P1 protein derived from M129 strain and the P1 protein derived from FH strain prepared in Comparative Example 1 as solid-phased antigens. Antibody-producing cells that showed an absorbance of 2.0 or more in the ELISA were selected.

A mouse (BALB/c, retired, Japan SLC, Inc.), inoculated with 2,6,10,14-tetramethylpentadecane (Sigma) in advance, was intraperitoneally inoculated with the anti-P1 antibody-producing cells, and the ascites was collected. The ascites was applied to a protein G column, and the obtained antibody was used as a purified anti-P1 antibody. Eventually, five clones of cells producing monoclonal antibodies against P1 protein derived from M129 and FH strains, respectively, were selected. All these monoclonal antibodies were of $IgG_1$ immunoglobulin isotype.

Example 4: Comparative Examination of Reactivity of Anti-P30 Antibody and Anti-P1 Antibody Reactivity of the anti-P30 antibodies prepared in Example 3 and the anti-P1 antibodies prepared in Comparative Example 2 was evaluated. Each of the antibodies produced in Example 2 and Comparative Example 2 was applied to a microplate to which the bacterial solutions of *Mycoplasma pneumoniae* M129 strain and FH strain prepared in Reference Example 1 and *Mycoplasma genitalium* were solid-phased at prescribed concentrations, followed by incubation at room temperature for 1 hour. Subsequently, the solution in each well was sucked and removed. After washing, a biotin-labeled anti-mouse antibody was added for reaction. After incubation for 1 hour, the solution in each well was sucked and removed. After washing, avidin-labeled horse radish peroxidase was added for reaction. A 3,3',5,5'-tetramethylbenzidine (TMBZ) solution was then added as a chromogenic substrate for reaction. The reaction was stopped with 2 N sulfuric acid. The absorbance was measured with a microplate reader (Biorad) at a main wavelength of 450 nm. The results are shown in Tables 1 to 3.

TABLE 1

Test of reactivity of anti-P30 antibody (sensitized with P30 protein derived from M129 strain)

| | *M. pneumoniae* | | |
| --- | --- | --- | --- |
| | M129 strain | FH strain | *M. genitalium* |
| BLA-001 | 2.632 | 2.126 | 0.040 |
| BLA-002 | 2.692 | 2.491 | 0.084 |
| BLA-003 | 2.883 | 2.790 | 0.080 |
| BLA-004 | 2.635 | 2.030 | 0.040 |
| BLA-005 | 2.171 | 2.137 | 0.056 |

TABLE 2

Test of reactivity of anti-P1 antibody (sensitized with P1 protein derived from M129 strain)

| | *M. pneumoniae* | | |
| --- | --- | --- | --- |
| | M129 strain | FH strain | *M. genitalium* |
| BLM-001 | 2.858 | 0.080 | 0.182 |
| BLM-002 | 2.528 | 2.961 | 0.070 |
| BLM-003 | 0.799 | 0.623 | 0.164 |
| BLM-004 | 1.697 | 0.120 | 0.099 |
| BLM-005 | 2.029 | 2.670 | 0.309 |

TABLE 3

Test of reactivity of anti-P1 antibody (sensitized with P1 protein derived from FH strain)

| | M. pneumoniae | | |
| --- | --- | --- | --- |
| | M129 strain | FH strain | M. genitalium |
| BLF-001 | 1.216 | 1.800 | 0.048 |
| BLF-002 | 2.238 | 2.957 | 1.968 |
| BLF-003 | 1.018 | 1.969 | 0.309 |
| BLF-004 | 2.036 | 2.987 | 0.254 |
| BLF-005 | 0.916 | 2.182 | 0.379 |

As obvious from Table 1, it was confirmed that the anti-P30 antibodies produced in Example 2 showed high reactivities with both *Mycoplasma pneumoniae* M129 strain and FH strain and did not show cross-reaction with the negative control, *Mycoplasma genitalium*.

In contrast, as obvious from Tables 2 and 3, it was revealed that the reactivities of the anti-P1 antibodies produced in Comparative Example 2 had bias on either M129 strain or FH strain of *Mycoplasma pneumoniae*. It is very probable that the bias of reactivity is caused by the P1 genotype, that is, a difference in the amino acid sequence between P1 proteins having different P1 genotypes is reflected to the reactivities of the monoclonal antibodies. In addition, a slight cross-reactivity with the negative control, *Mycoplasma genitalium*, was recognized.

It was accordingly demonstrated that P30 protein is commonly conserved in *Mycoplasma pneumoniae* and is a specific protein and further, monoclonal antibodies specifically recognizing P30 protein were obtained.

Example 5: Production of Immunochromatographic Test Strip Using Anti-P30 Antibody (1) Preparation of Anti-P30 Antibody Mice were intraperitoneally inoculated with hybridomas BLA-001 and BLA-002 prepared in Example 3, and the ascites obtained from each mouse was purified with protein G by an ordinary method to obtain IgG, which was used as an anti-P30 antibody.

(2) Preparation of Platinum-Gold Colloidal Particle Solution

Glassware to be used was all washed with aqua regia. Ultrapure water (390 mL) was boiled in a flask, and an aqueous chloroauric acid solution (30 mL, 1 L of the aqueous solution contains 1 g of gold, manufactured by Katayama Chemical Industries Co., Ltd.) was added to the boiling water. A 1 wt % aqueous sodium citrate solution (60 mL) was then added to the flask, and after 6 min and 45 sec, an aqueous chloroplatinic acid solution (30 mL, 1 L of the aqueous solution contains 1 g of platinum, manufactured by Wako Pure Chemical Industries, Ltd.) was added thereto. At 5 min after the addition of the aqueous chloroplatinic acid solution, a 1 wt % aqueous sodium citrate solution (60 mL) was added thereto, followed by reflux for 4 hours to obtain a platinum-gold colloidal suspension.

(3) Preparation of Platinum-Gold Colloid-Labeled Anti-P30 Antibody Solution

The clone BLA-002 obtained in the above section (1) was used as an anti-P30 antibody to be labeled with the platinum-gold colloid, and the labeling with the platinum-gold colloid was performed by the following procedure.

The anti-P30 antibody (1 μg in terms of protein weight, hereinafter, the weight of an antibody in terms of protein weight is simply shown by a numerical value of weight obtained by gravimetric analysis of the purified protein) and the platinum-gold colloidal solution (1 mL) described in the above section (2) were mixed, and the mixture was left to stand at room temperature for 2 minutes to allow all of the antibody to bind to the surfaces of the platinum-gold colloidal particles. An aqueous 10% bovine serum albumin (hereinafter, referred to as "BSA") solution was then added thereto at a final concentration of 1% in the platinum-gold colloidal solution to block all of the residual surfaces of the platinum-gold colloidal particles with BSA. Thus, a platinum-gold colloid-labeled anti-P30 antibody (hereinafter, referred to as "platinum-gold colloid-labeled antibody") solution was prepared. This solution was centrifuged (5600× G, for 30 min) to precipitate the platinum-gold colloid-labeled antibody, and the supernatant was removed to obtain a platinum-gold colloid-labeled antibody. This platinum-gold colloid-labeled antibody was suspended in a 50 mM tris hydrochloric acid buffer solution (pH 7.4) containing 10% saccharose, 1% BSA, and 0.5% Triton-X 100 to obtain a platinum-gold colloid-labeled antibody solution.

(4) Production of Immunochromatographic Test Strip Detecting P30 Protein of *Mycoplasma pneumoniae*

(4-1) Capturing Zone of Complex of P30 Protein of *Mycoplasma pneumoniae* and Platinum-Gold Colloid-Labeled Antibody An elongated strip-shaped nitrocellulose membrane with a size of 5 mm width and 36 mm length was provided as a membrane carrier 3 for chromatographic development of a chromatographic medium. 0.5 μL of a solution containing 1.0 mg/ml anti-P30 antibody was applied in a linear form to a position of 7.5 mm from the end on the starting point side of the chromatographic development of the membrane carrier 3 for chromatographic development. It was dried at room temperature, to form a capturing zone 31 for capturing a complex of the P30 protein and the platinum-gold colloid-labeled antibody. The applied anti-P30 antibody was the clone BLA-001 obtained in the above section (1).

(4-2) Platinum-Gold Colloid-Labeled Antibody-Impregnated Member

A strip-shaped glass fiber nonwoven fabric with a size of 5 mm×15 mm was impregnated with 37.5 μL of the platinum-gold colloid-labeled antibody solution, and then dried at room temperature, to obtain a platinum-gold colloid-labeled antibody impregnated member 2.

(4-3) Preparation of Immunochromatographic Test Strip

In addition to the membrane carrier 3 for chromatographic development and the labeled antibody-impregnated member 2, a cotton fabric as the sample-receiving member 5 and a filter paper as the absorbing member 4 were prepared. Then, a chromatographic test strip which was the same as FIG. 1 was prepared using these members.

(5) Test

The cultured bacterial solutions of M129 strain and FH strain of *Mycoplasma pneumoniae* prepared in Reference Example 1 were diluted with a sample extraction solution into a prescribed concentration to prepare each test sample. The test sample (120 μL) was dropwise added with a micropipette to the sample receiving member 5 of the test strip described in the above section (4) for chromatographic development by being left to stand at room temperature for 15 minutes. The captured amount of the complex of the P30 protein and the platinum-gold colloid-labeled antibody captured by the capturing zone 31 was observed with the naked eye. The captured amount was determined by evaluating the degree of blacking, which is proportional to the amount, with the naked eye and classified into the following five stages: − (no blacking), ± (slight blacking), + (clear blacking), ++ (noticeable blacking), and +++ (noticeable blacking).

Table 4 shows the results. As obvious from Table 4, it was revealed that P30 protein of *Mycoplasma pneumoniae* can be detected by immunochromatographic assay using two types of anti-P30 antibody. In addition, non-specific blacking was not observed in the blank.

TABLE 4

Reactivity with *Mycoplasma pneumoniae* M129 strain

|  |  | *M. pneumoniae* M129 strain |
|---|---|---|
| Concentration [CFU/ml] | Blank | − |
|  | $1 \times 10^6$ | + |
|  | $1 \times 10^7$ | ++ |

Comparative Example 4: Preparation of P1 Protein-Detecting Immunochromatographic Test Strip An immunochromatographic test strip was prepared using the anti-P1 antibodies reactive to both M129 strain and FH strain among the anti-P1 antibodies produced in Comparative Example 2, i.e., using BLM-002 as the antibody for labeling and BLF-001 as the antibody for the capturing zone, in accordance with the procedure for producing the immunochromatographic test strip as described in Example 3.

It was demonstrated that the immunochromatographic test strip using the anti-P1 antibody can detect *Mycoplasma pneumoniae* P1 protein.

Example 6: Comparative Reactivity Test of P30 Protein-Detecting Immunochromatographic Test Strip and P1 Protein-Detecting Immunochromatographic Test Strip The cultured bacterial solutions of M129 strain and FH strain of *Mycoplasma pneumoniae* prepared in Reference Example 1 were diluted with a sample extraction solution into a prescribed concentration to prepare each test sample. The test sample (120 µL) was dropwise added with a micropipette to the sample receiving member 5 of each immunochromatographic test strip for chromatographic development by being left to stand at room temperature for 15 minutes. The complex of the antigen and the platinum-gold colloid-labeled antibody captured by the capturing zone 31 was observed with the naked eye to determine the result. The captured amount was determined by evaluating the degree of blacking, which is proportional to the amount, with the naked eye and classified into the following five stages: − (no blacking), ± (slight blacking), + (clear blacking), ++ (noticeable blacking), and +++ (noticeable blacking). The results are shown in Table 5.

TABLE 5

Comparative reactivity test of P30 protein-detecting immunochromatographic test strip and P1 protein-detecting immunochromatographic test strip

|  |  | *M. pneumoniae* M129 strain | | *M. pneumoniae* FH strain | |
|---|---|---|---|---|---|
|  |  | anti-P30 antibody | anti-P1 antibody | anti-P30 antibody | anti-P1 antibody |
| Concentration [CFU/ml] | Blank | − | − | − | − |
|  | $1 \times 10^5$ | ± | − | + | − |
|  | $1 \times 10^6$ | + | − | ++ | ± |
|  | $1 \times 10^7$ | ++ | ± | +++ | + |
|  | $1 \times 10^8$ | +++ | + | +++ | ++ |

As obvious from Table 5, the P30 protein-detecting immunochromatographic test strip showed noticeable blacking for $1 \times 10^7$ CFU/mL of M129 strain and $1 \times 10^6$ CFU/mL of FH strain and showed clear blacking for $1 \times 10^6$ CFU/mL of M129 strain and $1 \times 10^5$ CFU/mL of FH strain.

In contrast, the P1 protein-detecting immunochromatographic test strip showed clear blacking for $1 \times 10^8$ CFU/mL of M129 strain and $1 \times 10^7$ CFU/mL of FH strain.

As obvious from the results shown in Table 5, the results of comparison of the bacterial concentrations of test samples at which the same degree of blacking was shown demonstrated that the detection sensitivity of the P30 protein-detecting immunochromatographic test strip was 100-times higher than that of the P1 protein-detecting immunochromatographic test strip in both reactivities with M129 strain and FH strain.

The results described above demonstrated that the P30 protein-detecting immunochromatographic test strip using the anti-P30 antibody can detect *Mycoplasma pneumoniae* with high sensitivity and specificity.

Example 6: Detection of *Mycoplasma pneumoniae* from Throat Swab

Throat swabs were collected from patients clinically suspected of infection with *Mycoplasma pneumoniae* with sterilized cotton swabs. The throat swabs were each verified as to whether the gene of *Mycoplasma pneumoniae* was present in the throat swab or not by the genetic test developed by National Institute of Infectious Diseases, Japan. Based on the results, seven samples in which the gene of *Mycoplasma pneumoniae* was detected and three samples in which the gene was not detected were selected from the collected throat swabs. The selected throat swabs were extracted with a sample extraction solution to prepare test samples. The test samples were subjected to detection of *Mycoplasma pneumoniae* using the P30 protein-detecting immunochromatographic test strip of the present invention.

The test sample (120 µL) was dropwise added with a micropipette to the sample receiving member 5 of the immunochromatographic test strip prepared in Example 3 for chromatographic development by being left to stand at room temperature for 15 minutes. The complex of the antigen and the platinum-gold colloid-labeled antibody captured by the capturing zone 31 was observed with the naked eye to determine the result.

Table 6 shows the results of the test.

TABLE 6

Detection of *Mycoplasma pneumoniae* from throat swab

| Sample No. | Immunochromatographic assay | Genetic test |
|---|---|---|
| 1 | + | + |
| 2 | + | + |
| 3 | − | − |
| 4 | − | − |
| 5 | + | + |
| 6 | + | + |
| 7 | + | + |
| 8 | − | − |
| 9 | + | + |
| 10 | + | + |

As obvious from Table 6, the results of detection by the P30 protein-detecting immunochromatographic test strip of the present invention all agreed with the results of the genetic test. Thus, it was demonstrated that *Mycoplasma pneumoniae* from throat swabs can be rapidly and simply detected by the P30 protein-detecting immunochromatographic test strip of the present invention.

Example 7: Detection of *Mycoplasma pneumoniae* from Throat Swab

Eighty one throat swabs were collected from 81 patients clinically suspected of infection with *Mycoplasma pneumoniae* by scraping the pharynges of the patients with sterilized cotton swabs. The cotton swabs used for collecting throat swabs were each subjected to extraction with 0.7 mL of a sample extraction solution to prepare test samples. The test samples were subjected to detection of *Mycoplasma pneumoniae* using the P30 protein-detecting immunochromatographic test strip of the present invention. Separately, as a control, a comparative performance test was conducted using the P1 protein-detecting immunochromatographic test strip. All of the collected clinical samples were subjected to a nucleic acid amplification test (PCR method) based on the genetic test developed by National Institute of Infectious Diseases, Japan to verify the presence of *Mycoplasma pneumoniae*.

The test sample (120 μL) was dropwise added with a micropipette to the sample receiving member 5 of the immunochromatographic test strip prepared in Example 3 for chromatographic development by being left to stand at room temperature for 15 minutes. The complex of the antigen and the platinum-gold colloid-labeled antibody captured by the capturing zone 31 was observed with the naked eye to determine the result. The results are shown in Table 7. In addition, as a control, the same procedure was performed using the immunochromatographic test strip prepared in Comparative Example 4, and the results were determined after the reaction. The results are shown in Table 8.

TABLE 7

Comparative test of P30 protein-detecting immunochromatographic test strip and nucleic acid amplification test (PCR method) for clinical sample

| | | Nucleic acid amplification test (PCR method) | | |
|---|---|---|---|---|
| | | Positive | Negative | Total |
| Example 3: P30 protein-detecting immunochromatographic test strip | Positive | 38 | 0 | 48 |
| | Negative | 10 | 33 | 43 |
| | Total | 48 | 33 | 81 |

When the nucleic acid amplification test was used as a standard, the P30 protein-detecting immunochromatographic test strip of the present invention showed a positive concordance rate (sensitivity) of 79.2%, a negative concordance rate (specificity) of 100.0%, and a total concordance rate of 87.7%.

TABLE 8

Comparative test of P1 protein-detecting immunochromatographic test strip and nucleic acid amplification test (PCR method) for clinical sample

| | | Nucleic acid amplification test (PCR method) | | |
|---|---|---|---|---|
| | | Positive | Negative | Total |
| Comparative Example 4: P1 protein-detecting immunochromatographic test strip | Positive | 8 | 0 | 8 |
| | Negative | 40 | 33 | 73 |
| | Total | 48 | 33 | 81 |

In contrast, the P1 protein-detecting immunochromatographic test strip as a Comparative Example showed a positive concordance rate (sensitivity) of 16.7%, a negative concordance rate (specificity) of 100.0%, and a total concordance rate of 50.6%.

As obvious from Tables 7 and 8, it was demonstrated that the results of detection by the P30 protein-detecting immunochromatographic test strip of the present invention well correlate to the results of the nucleic acid amplification test (PCR method). In addition, the present invention showed a high detection sensitivity compared to the P1 protein-detecting immunochromatographic test strip of a Comparative Example. This result demonstrated that the P30 protein-detecting immunochromatographic test strip of the present invention can detect *Mycoplasma pneumoniae* with high sensitivity and specificity at clinical sites.

INDUSTRIAL APPLICABILITY

The present invention provides an immunological method and a kit for detecting *Mycoplasma pneumoniae* using an antibody against P30 protein of *Mycoplasma pneumoniae*, and can rapidly and specifically diagnose infection with *Mycoplasma pneumoniae* without need of any specialized equipment or skill.

DESCRIPTION OF SYMBOLS

1 Adhesive sheet
2 Impregnated member
3 Membrane carrier

31 Capturing zone
32 Control capturing zone

4 Absorbing member
5 Sample receiving member

The invention claimed is:

1. A sandwich immunoassay kit for detecting *Mycoplasma pneumoniae* in a biological sample, at least comprising first and second antibodies against P30 protein of *Mycoplasma pneumoniae*, wherein at least one of the first and second antibodies is a monoclonal antibody recognizing an epitope of P30 protein present in a region of the amino acid sequence of SEQ ID NO: 2.

2. The sandwich immunoassay kit according to claim 1, wherein the sandwich immunoassay is an ELISA or immunochromatographic assay.

3. An immunochromatographic test strip for detecting *Mycoplasma pneumoniae* in a test sample, at least comprising first and second antibodies against P30 protein of *Mycoplasma pneumoniae* and a membrane carrier,
wherein the first antibody is previously immobilized at a predetermined position of the membrane carrier so as to form a capturing zone; and
the second antibody is labeled with an appropriate labeling substance and is provided at a position separated from the capturing zone so as to be chromatographically developed in the membrane carrier, whereby when the test sample is added to reach the above position, a complex of an antigen contained in the test sample and the second antibody is captured by the capturing zone,
wherein at least one of the first and second antibodies is a monoclonal antibody recognizing an epitope of P30 protein present in a region of the amino acid sequence of SEQ ID NO: 2, and
the test sample is a biological sample.

4. The immunochromatographic test strip according to claim 3, wherein the second antibody is labeled with a colloidal metal or a latex.

5. The immunochromatographic test strip according to claim 4, wherein the membrane carrier is a nitrocellulose membrane.

6. The sandwich immunoassay kit according to claim 1, wherein the biological sample is at least one selected from the group consisting of nasal cavity aspirate, nasal cavity swab, throat swab, sputum, saliva, and bronchial washings.

7. The immunochromatographic test strip according to claim 3, wherein the biological sample is at least one selected from the group consisting of nasal cavity aspirate, nasal cavity swab, throat swab, sputum, saliva, and bronchial washings.

* * * * *